United States Patent [19]
Brunstetter

[11] 3,939,827
[45] Feb. 24, 1976

[54] ERECTION AID FOR A PENIS
[75] Inventor: Frank H. Brunstetter, San Antonio, Tex.
[73] Assignee: Hi-Torr Inventions Corporation, San Antonio, Tex.
[22] Filed: Oct. 29, 1974
[21] Appl. No.: 518,295

[52] U.S. Cl. .................................................. 128/79
[51] Int. Cl.² ............................................ A61F 5/00
[58] Field of Search............. 128/79, 68, 68.1, 87 R

[56] References Cited
UNITED STATES PATENTS

| | | | |
|---|---|---|---|
| 1,362,398 | 12/1920 | Crawford et al. | 128/79 |
| 3,401,687 | 9/1968 | Hood | 128/79 |
| 3,495,588 | 2/1970 | Walters | 128/79 |
| 3,868,192 | 1/1959 | Dannen | 128/79 |

Primary Examiner—Lawrence W. Trapp
Attorney, Agent, or Firm—Reilly and Hancock

[57] ABSTRACT

The ventral surface of a penis between the base and the glans is supported by a semi-cylindrical splint or frame of a firm but bendable material, and the front end of the split is shaped to conform to and to lie directly behind the coronal ridge of the glans. A thin rubber cover encloses the remainder of the penis between the base and the glans and has its edges secured to the edges of the splint, or may be wrapped around the splint so that only one of its edges is secured to one of the edges of the splint with its other edge secured to a wrapped-around portion of the cover.

12 Claims, 8 Drawing Figures

U.S. Patent Feb. 24, 1976 3,939,827
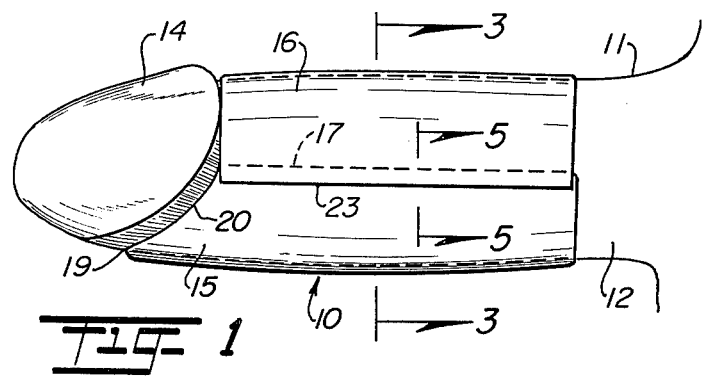
FIG. 1
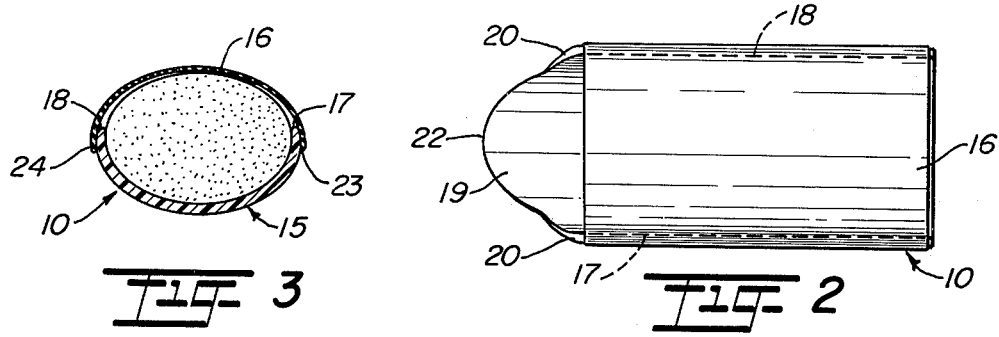
FIG. 3   FIG. 2
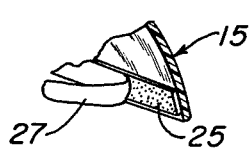   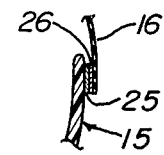
FIG. 4   FIG. 5
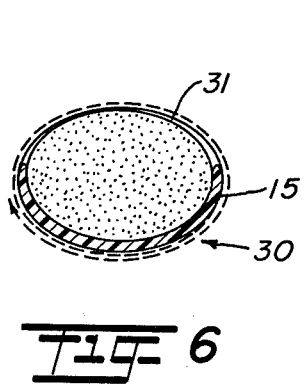
FIG. 6
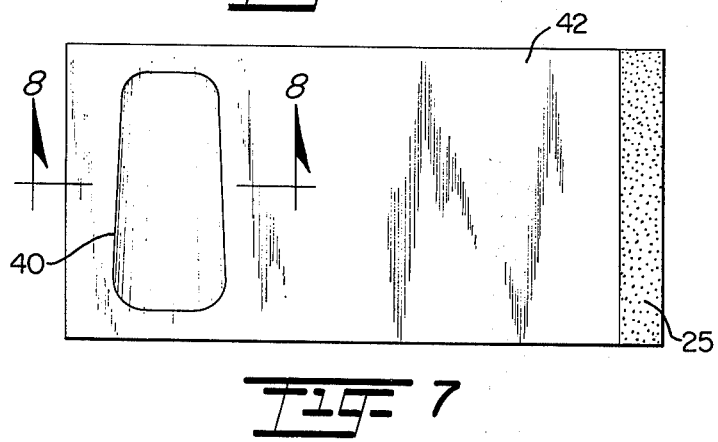
FIG. 7
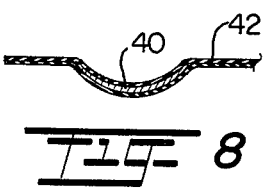
FIG. 8

ERECTION AID FOR A PENIS

Impotency in a male can be due to neurogenic or non-neurogenic difficulties. Various devices have previously been suggested to aid in obtaining an erection when the impotency is due to non-neurogenic causes.

In U.S. Pat. No. 1,216,099 to Falck, there is shown a device for assisting coitus by enclosing a penis within a semi-rigid sleeve with the glans of the penis exposed. The sleeve is split, and fits tightly around the penis. However, the device is rather cumbersome and relies upon a pocket within the sleeve to prevent compression of the large veins on the sides of the penis to permit some expansion of the penis. In addition, the sleeve is not fully expansible so that there could be restriction of the lumen of the urethra and of the blood flow through the penis to the glans.

U.S. Pat. No. 3,401,687 to Hood discloses an aid for obtaining an erection in which a supporter of resilient material is wrapped around the penis between the glans and the root or base of the penis. A cover of an elastic rubber is then disposed over the supporter. This arrangement tends to produce a light pressure on the corpus cavernosum at all times to restrict the blood flow to the glans of the penis. Furthermore, the cover also supplements this light pressure. Thus, the aid of the aforesaid Hood patent tends to unduly restrict the blood flow through the penis and could occlude the lumen of the urethra due to the light pressure applied by the supporter and the cover.

A surgical splint has been suggested in U.S. Pat. No. 3,495,588 to Walters to aid in inserting a penis into a female vagina irrespective of the extent of erection of the penis. The splint is formed of a plastic to give rigidity to the penis and has resilient sides causing the splint to have a grasping engagement with the shaft of the penis. After the penis is inserted in the vagina, the splint can be removed without removing the penis from the vagina. The tight fit of the splint of the aforesaid Walters patent tends to restrict the flow of blood through the penis. Furthermore, the splint could occlude the lumen of the urethra due to its tight fit on the penis. Thus, if one were not able to obtain a full erection with the splint of the Walters patent so that the splint could not be removed, the occlusion of the lumen of the urethra could prevent ejaculation.

The erection aid of the present invention satisfactorily overcomes the problems of the previously suggested devices in that there is no restriction of the flow of blood through the penis while still supporting the penis during insertion of the penis into the vagina and throughout coitus; and further permits the circumference of the penis to enlarge when erection occurs after penetration of the vagina is achieved. Thus, the full erection aid of the present invention permits a full erection without any restriction of blood flow through the penis or occlusion of the lumen of the urethra since the glans of the penis is fully exposed during penetration of the vagina and during coitus. The glans of the penis has many sensory nerve endings which aid in erection of the penis when stimulated and in a successful orgasm ultimately, the full exposure of the glans of the penis along with no interruption of blood flow through the penis, aids in obtaining a normal erection. Furthermore, this exposure of the glans aids in maintaining this erection if it should occur.

Preferably, the erection aid of the present invention accomplishes the foregoing through utilization of a splint or frame, which preferably has a semi-circular cross-section around the ventral surface of the penis and a cover of flexible material secured to the splint to retain the latter on the penis. The splint is of a firmness such that it does not pinch the penis whereby there is no occlusion of the lumen of the urethra and at the same time does not excessively bend during insertion of the penis into the vagina. The flexible material of the cover allows expansion and enlargement of the penis when a full erection is obtained.

It is therefore an object of the present invention to provide a novel and improved aid to obtain erection of a penis during intercourse.

Another object of the present invention is to provide an erection aid for a penis in which there is no restriction of the blood flow through the penis or any occlusion of the lumen of the urethra during intercourse.

It is a further object of the present invention to provide for the unique combination of an expandable first component and a non-expandable second component which can be removably positioned on the penis prior to intercourse to aid in penetrating the vagina and will not interfere with enlargement of the penis during intercourse and where such device is characterized by its ease of placement and removal, is snug-fitting and readily adjustable and will not irritate the vaginal walls during intercourse.

In its preferred form, an erection aid for a penis includes a support splint enclosing at least the bottom half of the penis and extending from adjacent the base to a point directly behind the glans of the penis. The splint is formed of a firm but bendable material to have a snug fit on the penis to support the penis for penetration into a vagina but without causing any restricton of blood flow through the penis. A thin resilient cover encloses the portion of the penis not enclosed by the splint with the cover extending from the rear end of the splint and also terminating behind the glans of the penis. The cover, which overlaps at least the edges of the splint, is removably and adjustably secured to the splint along mating longitudinal edges by suitable means, such as, adhesive strips.

Other objects, advantages and features of the present invention will become more readily apparent when taken together with the following detailed description taken in conjunction with the accompanying drawings, in which:

FIG. 1 is a side elevational view of a preferred form of erection aid in accordance with the present invention.

FIG. 2 is a top plan view of the preferred form of erection aid of the present invention.

FIG. 3 is a sectional view of the erection aid of the present invention taken along lines 3—3 of FIG. 1.

FIG. 4 is a fragmentary perspective view, partially in section, of a portion of one of the components of the erection aid of the present invention.

FIG. 5 is a fragmentary sectional view showing the edges of the two components of the erection aid of the present invention secured to each other and taken along lines 5—5 of FIG. 1.

FIG. 6 is a sectional view, similar to FIG. 3, and showing a modified form of the erection aid of the present invention.

FIG. 7 is an elevational view of another modified form of the present invention; and FIG. 8 is a sectional view taken about lines 8—8 of FIG. 7.

Referring to the drawings, and particularly to FIG. 1, there is shown by way of illustrative example an erection aid 10 disposed on a penis represented at 11. The erection aid 10 extends forwardly from base 12 of the penis 11 and terminates just behind the glans 14 or enlarged head of the penis 11.

The erection aid 10 includes a splint or frame 15 and a cover 16 removably secured together along mating longitudinal edges to be hereinafter described in snug, closely surrounding relation to the body or shaft of the penis.

The splint or frame 15 must be bendable while being firm and relatively thin. The degree of firmness or durometer of the material of the splint or frame 15 is such as to preclude excessive bending thereof during insertion into the vagina by the penis while still not causing any pinching or restriction of the penis before or after erection. The material of the splint or frame 15 also should be non-toxic and preferably is formed of a thin, firm, bendable rubber or medical grade plastic having the desired properties enumerated.

As shown in FIG. 3, the splint or frame 15 has a substantially semi-circular cross-section but may be dimensioned to encircle as much as three-fourths of the penis. The splint or frame 15 has its longitudinal edges 17 and 18 rounded so as to prevent any injury or irritation to the penis 11 or vagina during intercourse.

Since the coronal ridge of the glans 14 of the penis 11 extends or curves somewhat forwardly and downwardly toward the end, the splint or frame 15 has a forwardly extending portion 19 at its front end so as to follow the contour of the ridge. The forwardly extending portion 19 is formed as a continuation of the longitudinal edges 17 and 18 extending or curving forwardly and downwardly along a curved edge 20, which is rounded in cross-section as shown, and terminates in a forward extremity 22. In this way, the splint 15 will support the lower half of the penis 11 substantially along its entire length.

As further shown in FIG. 3, the cover 16 has a substantially semi-circular cross-section with diametrically opposed longitudinal edges 23 and 24 overlapping the longitudinal edges 17 and 18, respectively, of the splint 15. Preferably, the longitudinal edges 23 and 24 extend for the full length of the longitudinal edges 17 and 18 of the splint 15. The material of the cover 16 can be any flexible material which is non-toxic and has a medical grade quality. One suitable example of the material of the cover 16 is the expansible rubber material of which prophylactics are composed.

The cover 16 is retained on the splint 15 by detachable fastening or securing means preferably in the form of an adhesive strip 25 as shown in FIGS. 4 and 5 on the exterior of the splint or frame 15 along each of the edges 17 and 18, each of the strips 25 cooperating with an adhesive strip 26 on the inside of the cover 16 extending along each of the edges 23 and 24. Each of the adhesive strips 25 and 26 is formed of a non-toxic pressure-sensitive, adhesive strip of material which is permanently applied to each of the edges as described on the splint 15 and the cover 16. One suitable example of the adhesive is a reusable fabric adhesive strip sold under the trademark Velcro and characterized by being positively but releasably attachable, will permit some adjustment in overall size and which can be reused a number of times.

As shown in FIG. 4, the adhesive strip 25 of the splint or frame 15 has a removable protective strip 27 thereon. The removable protective strip 27 may be placed on the adhesive strip 25 when the splint or frame 15 is not in use. Although not shown, a similar protective strip is applied to each of the adhesive strips 26.

Accordingly, after the shaft of the penis 11 is disposed within the splint 15, the cover 16 is placed over the upper portion of the shaft of the penis 11, and the edges 23 and 24 of the cover 16 are secured to the mating edges 17 or 18 on the splint or frame 15 through the adhesive strips 25 and 26 either prior to or after placing the shaft of the penis 11 within the splint or frame 15.

The use of the splint or frame 15 insures that the lumen of the urethra is not occluded when the cover 16 has a snug fit around the penis 11. There also is no restriction of the flow of blood through the penis so as to permit complete erection.

Referring to FIG. 6, a modified form of erection aid 30 once again includes the frame or splint 15 for use in cooperation with a cover 31 which is wrapped around the splint or frame 15 more than once. In this arrangement, only one of the longitudinal edges of the cover 31 is secured to one of the longitudinal edges 17 and 18 of the splint or frame 15. The other longitudinal edge of the cover 31 is secured to a portion of the cover 31 wrapped around the splint or frame 15.

Preferably, the cover 31 is formed of the same material as the cover 16. Thus, by completely enclosing the splint or frame 15 with the cover 31, any possible irritation to the vagina by the splint or frame 15 is eliminated when using the erection aid 30.

The splint or frame 15 may be formed in different sizes and lengths so as to enable a precise fit and minimize any possibility of pinching the penis, even when fully erect. Most desirably, the splint or frame 15 is a reusable component of the erection aid 10, but the cover 16 or 31, which forms the other component of the erection aid 10, would not be reusable.

While the splint or frame 15 has been shown as having a semi-circular cross-section, it should be understood that the splint or frame 15 could enclose slightly more or less than one-half of the penis 11. It is only necessary that there be sufficient space between the edges 17 and 18 of the splint or frame 15 to enable expansion both of the length and circumference of the penis until a full erection is obtained. Thus, the splint or frame 15 may enclose as much as three-fourths of the penis 11 if desired without occluding the lumen of the urethra or restricting blood flow through the penis.

In the modified form of invention shown in FIGS. 7 and 8, a tapered form of splint 40 is embedded between layers of a flexible sheath which is defined by a cover strip or sheet 42. Here, the sheet 42 is of elongated generally rectangular configuration, preferably composed of a latex rubber material, and the splint is bonded or otherwise suitably affixed between the layers and adjacent to one end of the strip 42 as shown. In the same manner as shown in FIG. 6, the sheet 42 may be wrapped around the penis and the splint at least once to form the sheath, and the end opposite to that nearest the splint 40 is provided with an adhesive strip 25 to secure the erection aid snugly in place. In the modified form, it will be noted that the splint 40 is tapered in cross-section toward the side edges and also tapered forwardly; and the splint is of a composition possessing physical characteristics corresponding to those described with reference to the splint or frame 15 so as to assure a firm support but with a limited degree of pliability or flexibility so as to closely conform to the underside of the penis. Although the sheath 42 may be of tubular configuration, it is preferred to make it in the form of a rectangular sheet as shown so as to permit suitable adjustment for maximum comfort in use and ease of removal.

Among the advantages and features of this invention is that it can be easily and quickly placed in position, leaving the head or glans exposed and permitting full erection; also it insures that the lumen of the urethra is not closed or that there is any restricton of blood flow through the penis. After intercourse, the aid can be easily removed by separating either or both pairs of adhesive strips.

For purposes of exemplification, particular embodiments of the invention have been shown and described according to the best present understanding thereof. However, it will be apparent that changes and modifications in the arrangement and construction of the parts thereof may be resorted to without departing from the spirit and scope of the invention.

What is claimed is:

1. An erection aid for a penis including:
   a support splint adapted to extend along the ventral surface of the penis, said splint adapted to extend from adjacent to the base of the penis to the glans of the penis prior to erection and said splint being formed of a firm, bendable material;
   a thin, resilient cover adapted to enclose at least that portion of the penis not enclosed by said splint and adapted to extend from the rear end of said splint and terminating behind the glans of the penis;
   said cover including releasable retaining means to secure longitudinal edges of said cover to mating, longitudinally extending edges of said splint and being dimensioned together with said splint so as to effect a snug but non-tight fit on the penis to support the penis for penetration into a vagina without causing any restriction of blood flow through a penis.

2. The erection aid according to claim 1 in which the front end of said splint extends further at its bottom and is adapted to support the penis in conformity with the shape of the glans.

3. The erection aid according to claim 2 in which said cover is wrapped around said splint, said retaining means operative to secure one edge of said cover to one edge of said splint and the other edge of said cover to a wrapped-around portion of said cover.

4. The erection aid according to claim 1 in which said splint has a generally semi-circular cross-section and said splint has its edges rounded.

5. The erection aid according to claim 3 in which said splint has a generally semi-circular cross-section, and said splint has its edges rounded.

6. The erection aid according to claim 1 including releasable adhesive retaining means to secure longitudinal edges of said cover to mating longitudinal edges of said splint.

7. The erection aid according to claim 6 in which said splint has a semi-circular cross-section, and said splint has a front rounded edge.

8. The erection aid according to claim 1 in which said cover is adapted to be wrapped around said splint and around the shaft of the penis, and retaining means to secure one edge of said cover to one edge of said splint and the other edge of said cover to a wrapped-around portion of said cover.

9. The erection aid according to claim 8 in which said splint has a semi-circular cross-section and said splint has its front and longitudinal side edges rounded.

10. A penis erection aid comprising:
    a support splint adapted to extend along the ventral surface of the penis from adjacent ot the base of the penis to the glans of the penis prior to erection;
    a thin, resilient and stretchable sheath adapted to enclose at least that portion of the penis not enclosed by said splint, said sheath being in the form of a generally rectangular sheet of material adapted to be wrapped around the penis, and means adhesively securing the outer free end of said sheet against loosening or removal once wrapped in position around the penis; and
    said splint being embedded in and covered by said sheath so as to form an integral portion thereof, said sheath being dimensioned together with said splint so as to effect a snug fit on the penis to support the penis for penetration into a vagina without causing any restriction of blood flow through the penis.

11. A penis erection aid according to claim 10, said rectangular sheet of material being composed of layers of latex rubber, and said splint being embedded between the layers of the rectangular sheet.

12. A penis erection aid according to claim 10, said splint being composed of a firm, bendable material and being of arcuate configuration, said splint tapering laterally away from its midsection toward opposite lateral edges and further tapering forwardly from its midsection toward the leading end of the splint.

* * * * *